(12) United States Patent
Ishikawa

(10) Patent No.: US 11,330,972 B2
(45) Date of Patent: May 17, 2022

(54) OBLIQUE-VIEWING ENDOSCOPE

(71) Applicant: OLYMPUS CORPORATION, Tokyo (JP)

(72) Inventor: Shinya Ishikawa, Fuchu (JP)

(73) Assignee: OLYMPUS CORPORATION, Tokyo (JP)

(*) Notice: Subject to any disclaimer, the term of this patent is extended or adjusted under 35 U.S.C. 154(b) by 53 days.

(21) Appl. No.: 16/924,631

(22) Filed: Jul. 9, 2020

(65) Prior Publication Data
US 2020/0337538 A1 Oct. 29, 2020

Related U.S. Application Data

(63) Continuation of application No. PCT/JP2018/035218, filed on Sep. 21, 2018.

(30) Foreign Application Priority Data

Jan. 11, 2018 (JP) .............................. JP2018-002611

(51) Int. Cl.
*A61B 1/05* (2006.01)
*A61B 1/00* (2006.01)
*A61B 1/06* (2006.01)

(52) U.S. Cl.
CPC ............ *A61B 1/05* (2013.01); *A61B 1/00096* (2013.01); *A61B 1/00124* (2013.01); *A61B 1/00179* (2013.01); *A61B 1/0653* (2013.01)

(58) Field of Classification Search
CPC combination set(s) only.
See application file for complete search history.

(56) References Cited

U.S. PATENT DOCUMENTS 4,918,521 A * 4/1990 Yabe .................. A61B 1/00177
600/109
6,494,739 B1 * 12/2002 Vivenzio ............ H01R 13/5804
358/473

FOREIGN PATENT DOCUMENTS

| JP | H09-122070 A | 5/1997 |
| JP | H11-89794 A | 4/1999 |
| JP | H11-276424 A | 10/1999 |
| JP | 2006-239312 A | 9/2006 |

OTHER PUBLICATIONS

International Search Report dated Dec. 11, 2018 issued in PCT/JP2018/035218.

* cited by examiner

*Primary Examiner* — Michael J Carey
*Assistant Examiner* — Amy Kristina Polanecki
(74) *Attorney, Agent, or Firm* — Scully, Scott, Murphy & Presser, P.C.

(57) ABSTRACT

An oblique-viewing endoscope includes: an endoscope axis that is a longitudinal direction of an endoscope distal end portion; an optical axis of a lens, the optical axis being an observing direction, the endoscope axis and the optical axis being disposed to form a predetermined inclination angle with respect to each other; a rectangular semiconductor package including an imaging sensor configured to convert an optical image formed by the lens to an image signal, and a terminal formed on a back face of the semiconductor package; and a rigid substrate including a semiconductor package mounting area in which the semiconductor package is mounted, an electronic component mounting area in which an electronic component is mounted, and a cable mounting area in which a cable is mounted.

7 Claims, 7 Drawing Sheets

OBLIQUE-VIEWING ENDOSCOPE

CROSS-REFERENCE TO RELATED APPLICATION

This application is a continuation of PCT International Application No. PCT/JP2018/035218 filed on Sep. 21, 2018, which designates the United States, incorporated herein by reference, and which claims the benefit of priority from Japanese Patent Application No. 2018-002611, filed on Jan. 11, 2018, incorporated herein by reference.

BACKGROUND

1. Technical Field

The present disclosure relates to an oblique-viewing endoscope for observing an interior of a subject from an oblique direction.

2. Related Art

In the related art, an endoscope that can be inserted into a subject for observing a part to be inspected and, if necessary, for carrying out various types of treatments use of a treatment instrument inserted into a treatment instrument channel is used widely. As the endoscope, besides a front-viewing endoscope for observing a front, a side-viewing and oblique-viewing endoscopes with lens units disposed in different orientations are used depending on an observing direction.

As the side-viewing endoscope, there is an endoscope as proposed in JP 2006-239312 A, for example, in which a lens unit is disposed such that an optical axis of the lens unit becomes inclined with respect to an endoscope axis, an imaging sensor is disposed parallel to the lens unit (such that a light receiving face of the imaging sensor becomes orthogonal to the optical axis of the lens unit), and an end portion of a flexible printed circuit board mounted with electronic components and cables and disposed parallel to the endoscope axis is bent to thereby be connected to a terminal of the imaging sensor.

As the oblique-viewing endoscope, there is an endoscope as proposed in JP H09-122070 A, for example, in which light from a lens unit disposed such that an optical axis becomes inclined with respect to an endoscope axis enters, through a prism, a charge-coupled device (CCD) package disposed parallel to the endoscope axis.

SUMMARY

In some embodiments, an oblique-viewing endoscope includes: an endoscope axis that is a longitudinal direction of an endoscope distal end portion; an optical axis of a lens, the optical axis being an observing direction, the endoscope axis and the optical axis being disposed to form a predetermined inclination angle with respect to each other; a rectangular semiconductor package including an imaging sensor configured to convert an optical image formed by the lens to an image signal, and a terminal formed on a back face of the semiconductor package; and a rigid substrate including a semiconductor package mounting area in which the semiconductor package is mounted, an electronic component mounting area in which an electronic component is mounted, and a cable mounting area in which a cable is mounted, the rigid substrate being a multi-layer substrate with a layered direction parallel to a plane including the endoscope axis and the optical axis, the semiconductor package mounting area of the rigid substrate being formed on an inclined face orthogonal to the optical axis, at least a part of the electronic component mounting area being disposed on a triangular side face of the rigid substrate surrounded with the inclined face, a projection plane of the inclined face in a horizontal direction, and a projection plane of the inclined face in a vertical direction.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
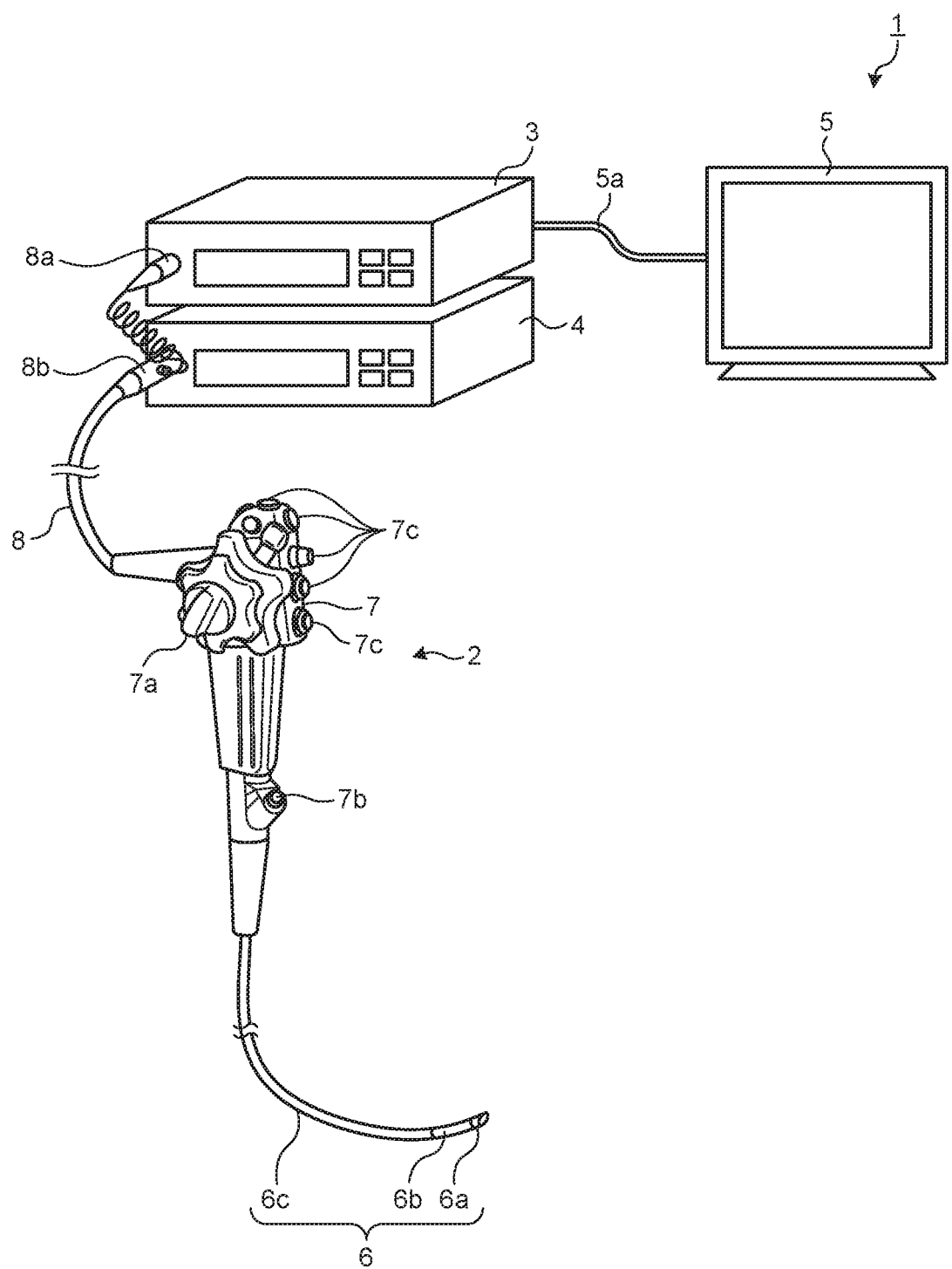
FIG. 1 schematically illustrates a whole structure of an endoscope system according to a first embodiment of the disclosure.

In the following description, endoscope systems respectively including imaging units will be described as modes for carrying out the disclosure (hereinafter referred to as "embodiments"). The embodiments are not intended to limit the disclosure. In the drawings, the same portions are provided with the same reference signs. The drawings are schematic representations and it should be noted that relationships between thicknesses and widths of respective members, ratios between the respective members, and the like are different from actual ones. The drawings are different from each other in dimensions and ratios of some portions.

First Embodiment

FIG. 1 schematically illustrates a whole structure of an endoscope system 1 according to the first embodiment of the disclosure. As illustrated in FIG. 1, the endoscope system 1 according to the first embodiment includes an endoscope 2 that is inserted into a subject, images an interior of the subject, and generates an image signal of the interior of the subject, an information processing device 3 that performs predetermined image processing of the image signal obtained by the imaging by the endoscope 2 and controls respective portions of the endoscope system 1, a light source device 4 that generates illumination light for the endoscope 2, and a display device 5 that displays, as an image, the image signal after the image processing by the information processing device 3.

The endoscope 2 is an oblique-viewing endoscope for observing the interior of the subject from an oblique direction and includes an insertion portion 6 that is inserted into the subject, an operating portion 7 that is on a side of a proximal end portion of the insertion portion 6 and that is grasped by a surgeon, and a universal cord 8 that is flexible and extended by use of the operating portion 7.

The insertion portion 6 is realized by use of illumination fibers, electric cables, optical fibers, and the like. The insertion portion 6 has a distal end portion 6a into which the imaging unit (described later) is mounted, a curving portion 6b formed by a plurality of curving pieces and capable of curving, and a flexible tube 6c provided on a side of a proximal end portion of the curving portion 6b and having flexibility. The distal end portion 6a is provided with a light guide cable 20 (see FIG. 2) that illuminates the interior of the subject through an illumination lens 21 (see FIG. 2), an observing unit that captures the interior of the subject, an aperture that opens a channel for treatment instruments, and an air insufflation/water insufflation nozzle (not illustrated).

The operating portion 7 has a curving knob 7a for curving the curving portion 6b in a vertical direction and a left-right direction, a treatment instrument insertion portion 7b from which the treatment instruments such as a bioptome and a laser scalpel are inserted into a body cavity of the subject, and a plurality of switches 7c for operating peripheral devices such as the information processing device 3, the light source device 4, an air insufflator, a water insufflator, a gas insufflator, and the like. The treatment instrument inserted from the treatment instrument insertion portion 7b passes through the channel for the treatment instruments formed inside and appears from the aperture in the distal end of the insertion portion 6.

The universal cord 8 is formed by illumination fibers, cables, or the like. The universal cord 8 bifurcates at a proximal end into two, an end portion of one of which is a connector 8a and a proximal end of the other of which is a connector 8b. The connector 8a is attachable to and detachable from a connector of the information processing device 3. The connector 8b is attachable to and detachable from the light source device 4. The universal cord 8 propagates the illumination light emitted from the light source device 4 to the distal end portion 6a via the connector 8b and the illumination fibers. The universal cord 8 transmits the image signal obtained by imaging by the imaging unit (described later) to the information processing device 3 via the cable and the connector 8a.

The information processing device 3 carries out the predetermined image processing of the image signal output from the connector 8a and controls the entire endoscope system 1.

The light source device 4 is formed by a light source that emits the light, a condenser lens, and the like. The light source device 4 emits the light from the light source and supplies the light to the endoscope 2 connected to the light source device 4 by the connector 8b and the illumination fibers of the universal cord 8 as the illumination light for the interior of the subject that is an imaging target under a control of the information processing device 3.

The display device 5 is formed by a display and the like using liquid crystal or organic electro luminescence (EL). The display device 5 displays various kinds of information including the image subjected to the predetermined image processing by the information processing device 3 and received via a video cable 5a. Thus, the surgeon can observe and determine properties of a desired position of the interior of the subject by operating the endoscope 2 while watching the images (in-vivo images) displayed on the display device 5.

Figure 2:
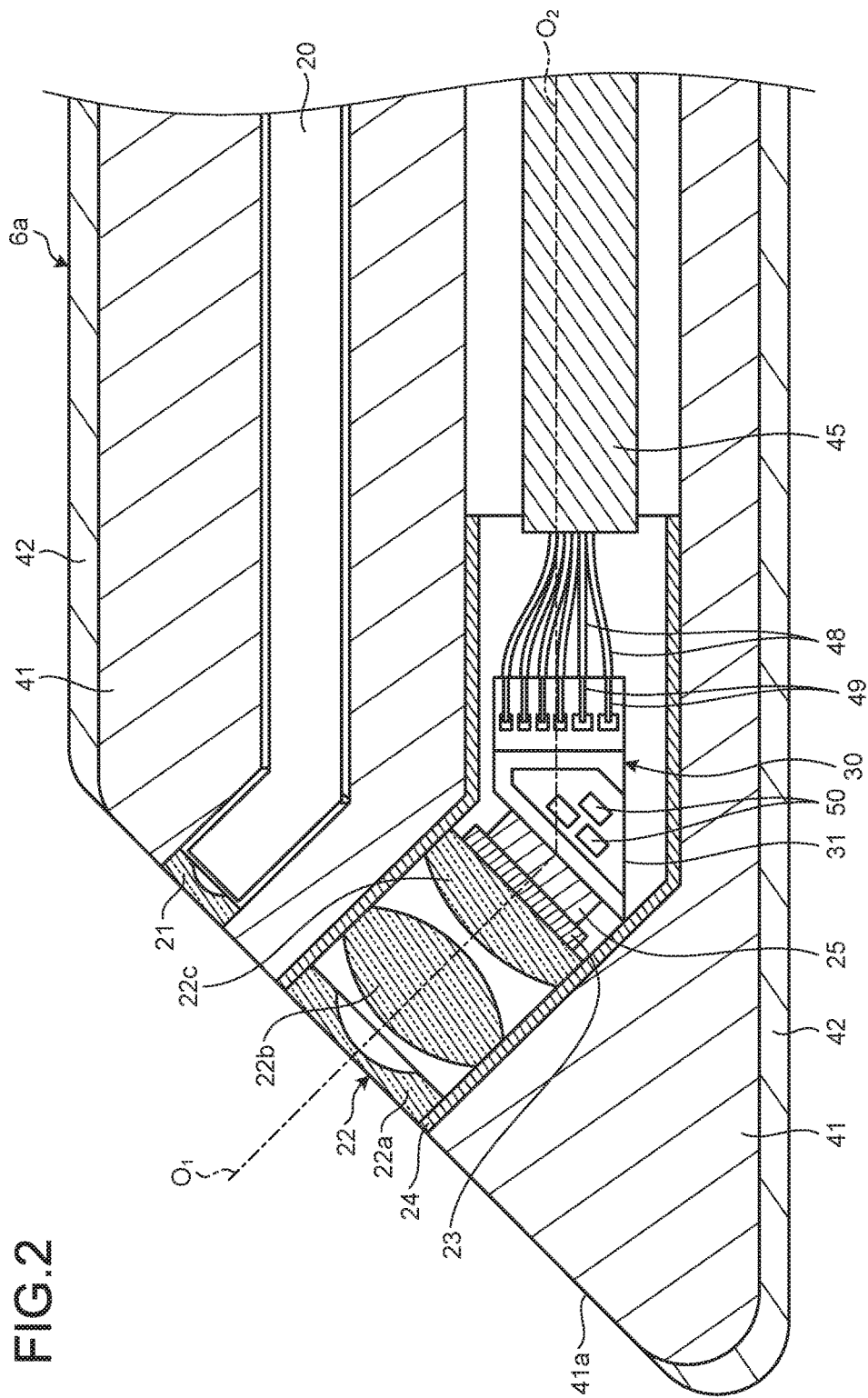
FIG. 2 is a sectional view of an endoscope distal end portion illustrated in FIG. 1.
Figure 3:
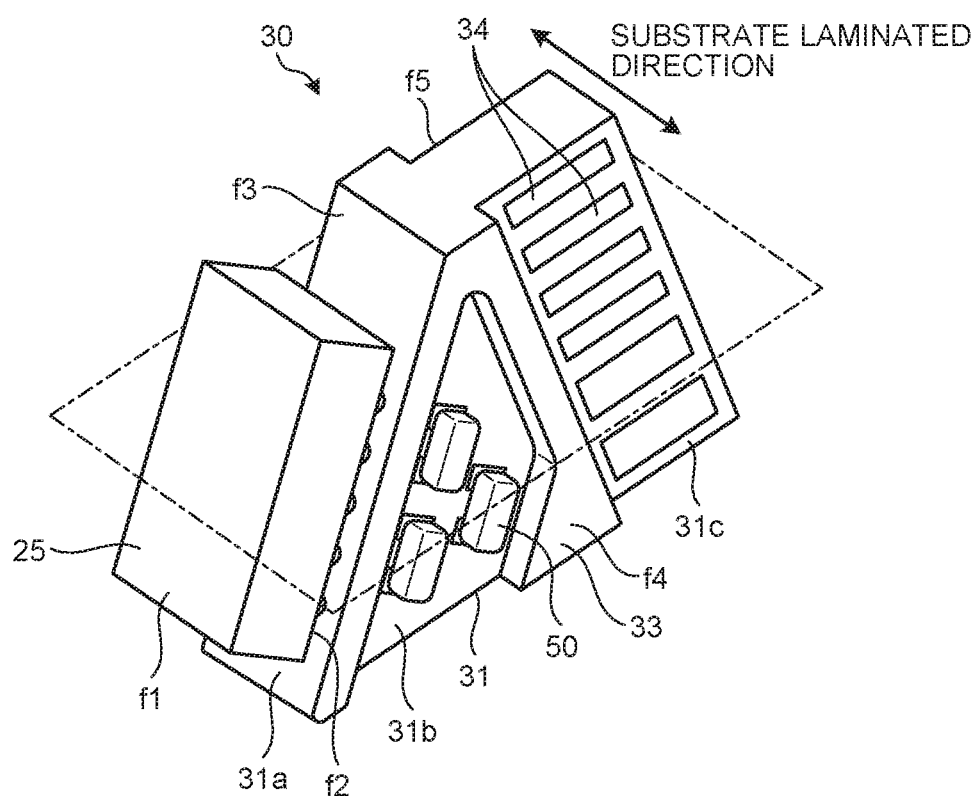
FIG. 3 is a perspective view of an imaging unit illustrated in FIG. 2.
Figure 4A:
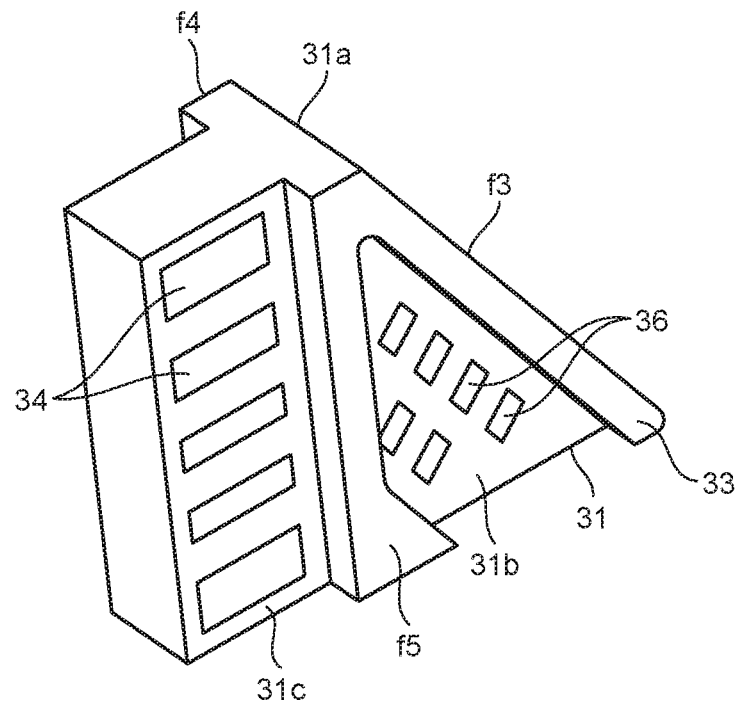
FIGS. 4A and 4B are perspective views of a rigid substrate in FIG. 3.
Figure 4B:
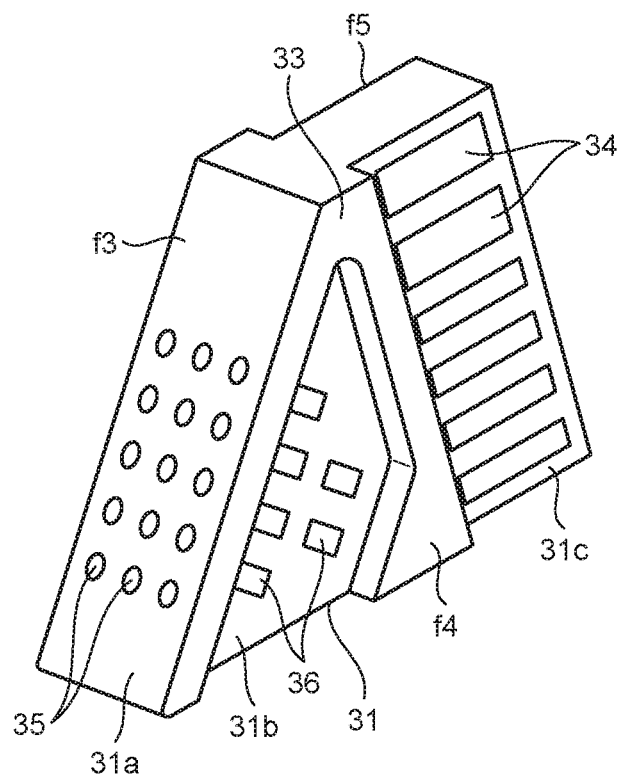
Figure 5:
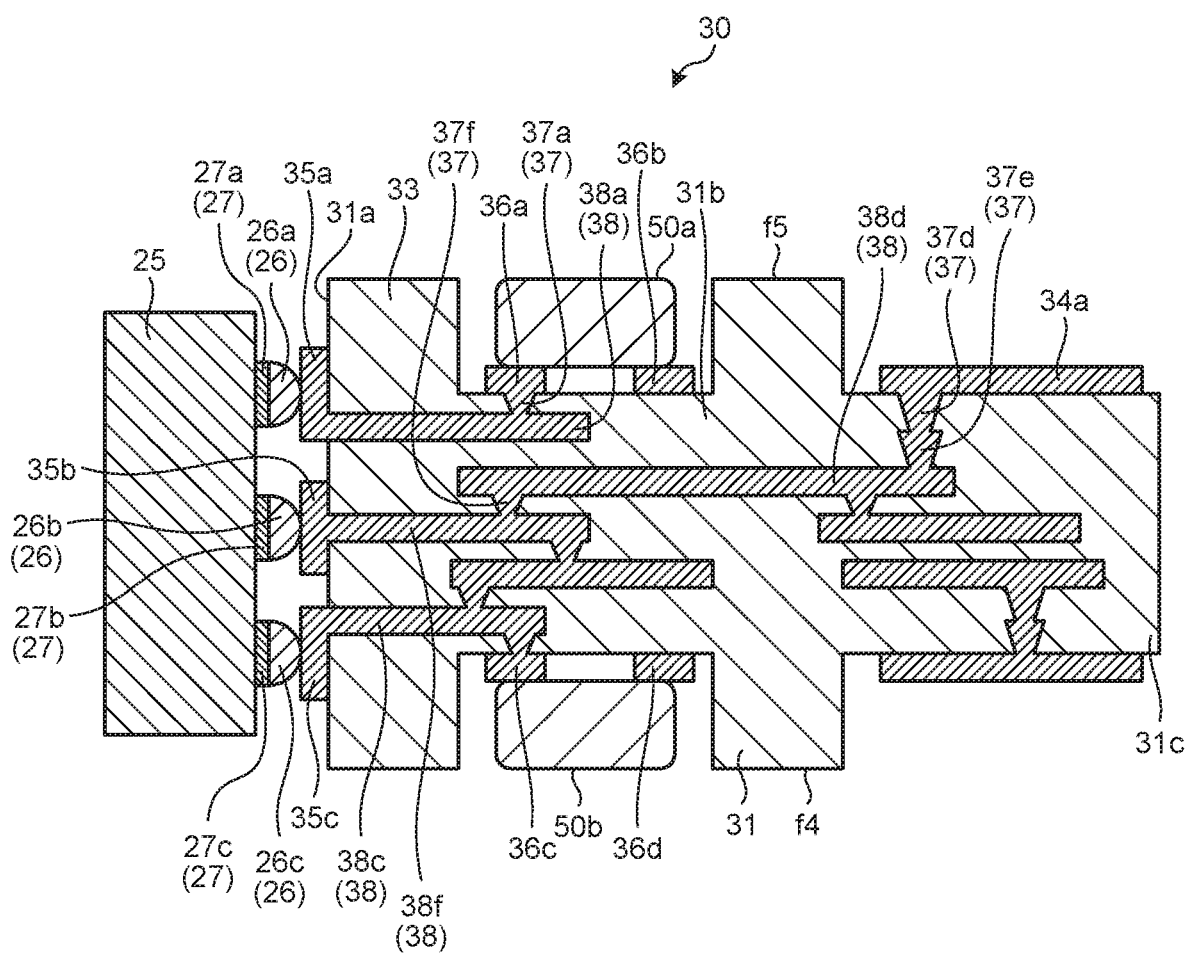
FIG. 5 is a sectional view of the imaging unit in FIG. 3.

Next, a structure of the distal end portion 6a of the endoscope 2 will be described in detail. FIG. 2 is a sectional view of the distal end portion 6a of the endoscope 2. FIG. 3 is a perspective view of an imaging unit 30 illustrated in FIG. 2. FIGS. 4A and 4B are perspective views of a rigid substrate 31 in FIG. 3. FIG. 5 is a sectional view of the imaging unit 30 in FIG. 3 (the sectional view in a plane including a one-dot chain line). FIG. 2 is the sectional view in a plane parallel to an optical axis $O_1$ of a lens unit 22 and an endoscope axis $O_2$ (described later) of the endoscope 2 (the plane including the optical axis $O_1$ of the lens unit and the endoscope axis $O_2$).

An imaging device has the lens unit 22 and the imaging unit 30 disposed on a side of a proximal end of the lens unit 22. A distal end portion main body 41 is formed by a rigid member for forming an inner space for housing the imaging device. An outer peripheral portion of the distal end portion main body 41 is covered with a soft cover tube 42. A distal end face 41a of the distal end portion main body 41 is formed as an inclined face.

The lens unit 22 has a plurality of objective lenses 22a, 22b, and 22c and a lens holder 24 that holds the objective lenses 22a to 22c and the lens holder 24 is fixed by being inserted and fitted into the distal end portion main body 41 to thereby fix the lens unit 22 to the distal end portion main body 41. The optical axis $O_1$ of the lens unit 22 is disposed in such a manner as to form a predetermined angle with the endoscope axis $O_2$, which enables the observation of the interior of the subject from the oblique direction.

The imaging unit 30 includes a semiconductor package 25 in a rectangular shape and having an imaging sensor that generates an electric signal by photoelectrically converting an optical image received by a face f1 as a light receiving face and sensor electrodes 27 formed on a face f2 as a back face. The imaging unit 30 also includes a rigid substrate 31 having a semiconductor package mounting area 31a in which the semiconductor package 25 is mounted, electronic component mounting areas 31b in which electronic components 50 are mounted, and cable mounting areas 31c in which signal cables 48 are mounted. The semiconductor package 25 is fixed by bonding to the objective lens 22c with a cover glass 23 interposed therebetween.

The light collected by the lens unit 22 enters the face f1 that is the light receiving face. The sensor electrodes 27 are formed on the face f2 (the back face) of the semiconductor package 25. The semiconductor package 25 is preferably a chip size package (CSP) that is formed by subjecting an imaging sensor chip, while in a state of a wafer, to trace, electrode formation, resin sealing, and dicing, the resulting semiconductor package 25 being of the same size as the imaging sensor chip.

The rigid substrate 31 is a multi-layer substrate formed by layering a plurality of substrates, on which traces are formed, in a direction indicated by an arrow in FIG. 3 (the direction parallel to the plane including the endoscope axis $O_2$ and the optical axis $O_1$ (by layering the plurality of substrates parallel to a side face f4 and a side face f5). Inside the rigid substrate 31, vias 37 that electrically connect traces 38 on the layered substrates are formed. If the rigid substrate 31 is formed as the multi-layer substrate, it is easy to dispose a wall portion 33 and the like of the electronic component mounting areas 31b (described later). However, the rigid substrate 31 is not limited to the multi-layer substrate. As the layered substrates, ceramic substrates, glass epoxy substrates, glass substrates, silicon substrates, and the like may be employed.

The semiconductor package mounting area 31a of the rigid substrate 31 is formed on an inclined face f3 orthogonal to the optical axis $O_1$ of the lens unit 22. The inclined face f3 is inclined at an angle equal to an inclination angle of the distal end face 41a of the distal end portion main body 41 in which the lens unit 22 is disposed. In the semiconductor package mounting area 31a, connection lands 35 to which the semiconductor package 25 is connected are formed and the semiconductor package 25 is electrically and mechanically connected to the connection lands 35 with the sensor electrodes 27 of the semiconductor package 25 and junction members 26 such as solder balls interposed therebetween. Besides the solder balls, the junction members 26 may be metal core solder balls, resin core solder balls, Au bumps, or the like. The connection lands 35 are formed by screen printing, spattering, metal deposition, or the like.

The electronic component mounting areas 31b are disposed on the side faces f4 and f5 of the rigid substrate 31 surrounded with the inclined face f3 on which the semiconductor package mounting area 31a is formed, a projection plane of the inclined face f3 in a horizontal direction, and a projection plane of the inclined face f3 in a vertical direction. In the first embodiment, the electronic component mounting areas 31b are disposed on the triangular side faces surrounded with the inclined face f3, the projection plane of the inclined face f3 in the horizontal direction, and the projection plane of the inclined face f3 in the vertical direction. By disposing at least parts of the electronic component mounting areas 31b in these areas, it is possible to reduce a length of the rigid substrate 31 in a direction of the endoscope axis $O_2$ to thereby shorten a rigid portion of the endoscope 2.

In the electronic component mounting areas 31b, electronic component connection lands 36 to which the electronic components 50 forming a drive circuit for the imaging sensor are connected are formed and the electronic component connection lands 36 are electrically and mechanically connected to the electronic components 50 with junction members such as solder interposed therebetween. The wall portion 33 is formed on sides of the triangular shapes of the electronic component mounting areas 31b close to the inclined face f3 and the cable mounting areas 31c on the proximal end side. The wall portion 33 is designed to have a height greater than or equal to heights of the electronic components 50 in mounted states. If the wall portion 33 has the height greater than or equal to the heights of the electronic components 50, it is possible to relax stress applied to the electronic components 50 from adhesive disposed on peripheries. Although the wall portion 33 is provided on two sides of the triangular shapes in the first embodiment, the wall portion 33 may be provided on one side or three sides in the electronic component mounting areas 31b, electronic components other than the electronic components forming the drive circuit for the imaging sensor may be mounted. Although the electronic components 50 are mounted on surfaces of the side faces f4 and f5 of the rigid substrate 31, the electronic components 50 may be mounted in the rigid substrate 31 as long as the electronic components 50 are mounted in a triangular portion surrounded with the inclined face f3, the projection plane of the inclined face f3 in the horizontal direction, and the projection plane of the inclined face f3 in the vertical direction.

The electronic component connection lands 36 to which the electronic components 50 are connected are preferably disposed near the sensor electrodes 27 of the semiconductor package 25 to which the electronic components are connected by the traces 38 and the vias 37. For example, an electronic component 50a mounted on the side face f5 in FIG. 5 is connected to a sensor electrode 27a by an electronic component connection land 36a, a via 37a, a trace 38a, a connection land 35a, and a junction member 26a. In order to make a length of the trace 38a short, the electronic component connection land 36a is disposed near the sensor electrode 27a. Thus, a distance between the imaging sensor and the electronic component 50a becomes short, which reduces an impedance and enables stable driving of the imaging sensor. As a result, it is possible to obtain high-quality images. Similarly, for an electronic component 50b mounted on the side face f4, an electronic component connection land 36c is disposed near a sensor electrode 27c so as to make a length of a trace 38c short.

The cable mounting areas 31c are disposed on the side of the proximal ends of the electronic component mounting areas 31b. Cable connection lands 34 to which cores 49 of the signal cables 48 are connected are formed in the cable mounting areas 31c and the signal cables 48 are electrically and mechanically connected to the cable connection lands 34 by the cores 49 and junction members such as solder.

The cable connection lands 34 to which the signal cables 48 are connected are preferably disposed, in the cable mounting areas 31c, near a sensor electrode 27b of the semiconductor package 25 to which the signal cables 48 are connected. For example, a cable connection land 34a in FIG. 5 to which the signal cable 48 is connected is connected to the sensor electrode 27b by a via 37d, a via 37e, a trace 38d, a via 37f, a trace 38f, a connection land 35b, and a connection member 26b. The cable connection land 34a is disposed in the cable mounting area 31c in such a manner as to make the sum of lengths of the traces 38d, 38f short. Although the cable connection land 34a is provided on a different layer from the sensor electrode 27b in FIG. 5, the cable connection land 34a may be formed on a substrate of a layer near the sensor electrode 27b in order to reduce the number of vias necessary for connection to the sensor electrode 27b.

Proximal ends of the signal cables 48 extend toward the proximal end of the insertion portion 6. A signal cable bundle 45 is inserted into and disposed in the insertion portion 6 and extends to the connectors 8a and 8b via the operating portion 7 and the universal cord 8 illustrated in FIG. 1.

The optical image formed by the objective lenses 22a to 22c of the lens unit 22 is converted to the image signal by the imaging sensor disposed at an image forming position of the objective lenses 22a to 22c and sent to the information processing device 3 via the rigid substrate 31 and the signal cables 48. In the first embodiment, the rigid substrate 31 is provided with the inclined face f3 inclined at the angle equal to the inclination angle of the distal end face 41a of the distal end portion main body 41 and the semiconductor package 25 is mounted on the inclined face f3. Because the rigid substrate 31 is rigid, it is easy to treat the rigid substrate 31, use of a prism and the like in a special shape is unnecessary, and distortion correction is unnecessary, which reduces cost. In the first embodiment, the triangular side face portions surrounded with the inclined face f3 of the rigid substrate 31, the projection plane of the inclined face f3 in the horizontal direction, and the projection plane of the inclined face f3 in the vertical direction serve as the electronic component mounting areas 31b. Therefore, it is possible to make the length of the rigid substrate 31 in the direction of the endoscope axis $O_2$ short to thereby obtain the oblique viewing endoscope that can be miniaturized.

Figure 6A:
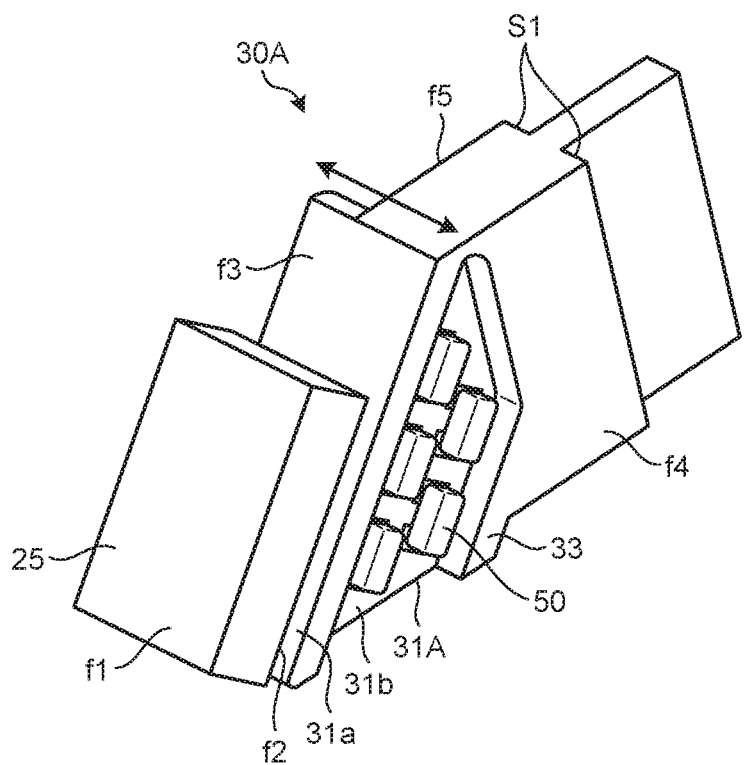
FIGS. 6A and 6B are perspective views of an imaging unit according to a modification of the first embodiment of the disclosure.
Figure 6B:
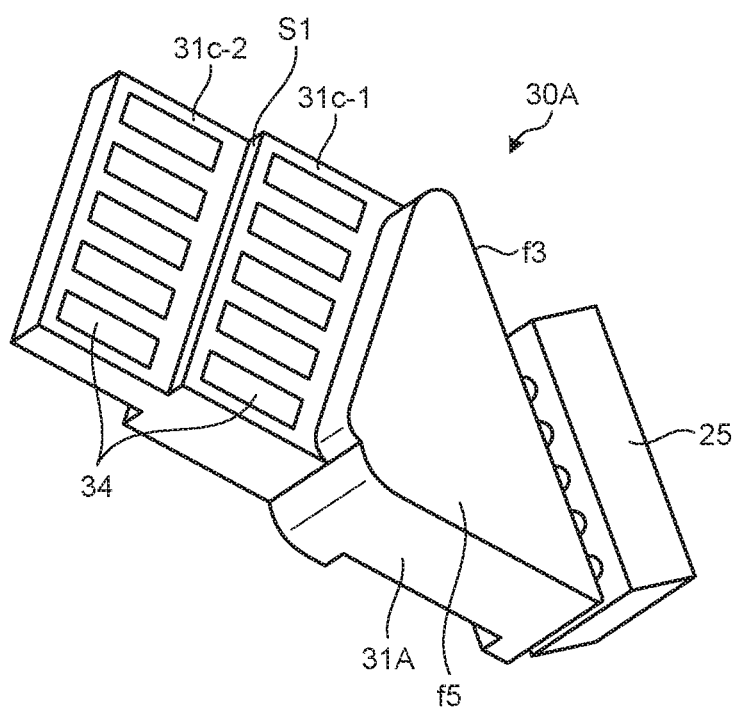

Although the electronic component mounting areas 31b and the cable mounting areas 31c are formed on the opposite side faces f4 and f5 of the rigid substrate 31 in the first embodiment, the electronic component mounting area 31b and the cable mounting area 31c may be formed on only one of the side faces. FIGS. 6A and 6B are perspective views of the imaging unit 30A according to a modification of the first embodiment of the disclosure.

In the imaging unit 30A, an electronic component mounting area 31b is formed on a side face f4 of a rigid substrate 31A and cable mounting areas 31c-1, 31c-2 are formed on a side face f5. Between the cable mounting area 31c-1 and the cable mounting area 31c-2, a step S1 is provided. By separately disposing the electronic component mounting area 31b and the cable mounting areas 31c-1, 31c-2 on opposite side faces, the electronic components 50 and the signal cables 48 can be respectively mounted at one time. By dividing the cable mounting area into the areas 31c-1 and 31c-2 by use of the step S1, it is possible to easily connect the large number of signal cables. The rigid substrate 31A has a smaller diameter on a proximal end side due to the steps S1, which reduces an influence of stress applied to connected portions due to curving and the like of an endoscope. Although the side face f4 of the rigid substrate 31A is provided with the step S1 similarly to the side face f5, the side face f4 does not necessarily have to be provided with the step S1.

In the first modification, similarly, by disposing a part of the electronic component mounting area 31b on the triangular side face surrounded with an inclined face f3, a projection plane of the inclined face f3 in a horizontal direction, and a projection plane of the inclined face f3 in a vertical direction, it is possible to reduce a length of the rigid substrate 31A in a direction of an endoscope axis $O_2$ to thereby shorten a rigid portion of the endoscope.

Second Embodiment

Figure 7A:
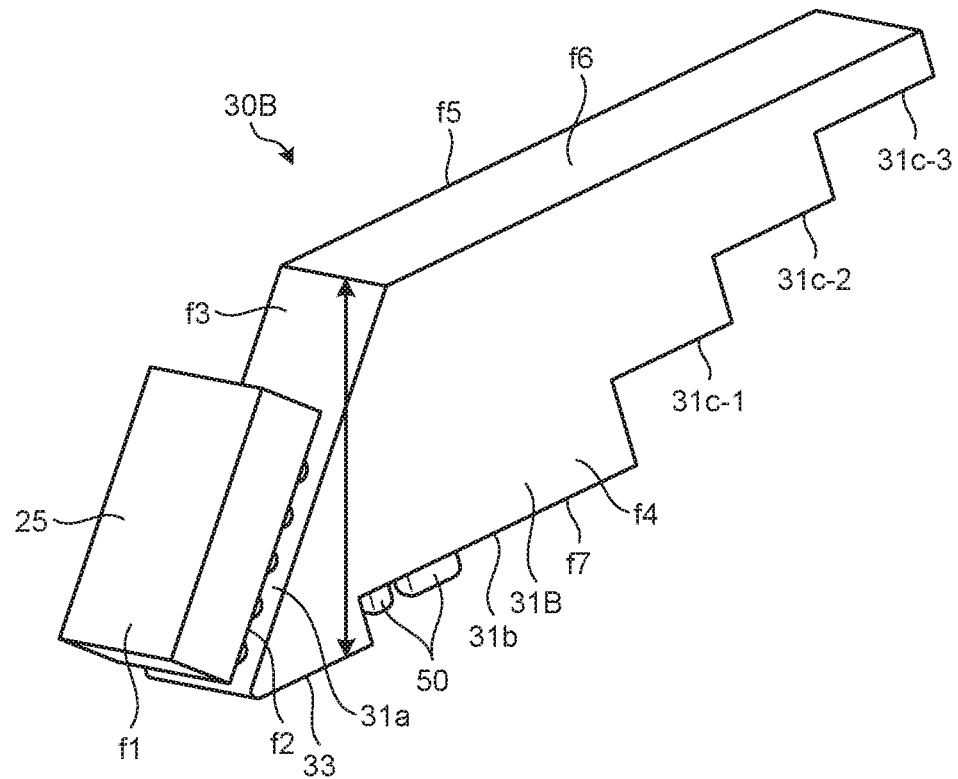
FIGS. 7A and 7B are perspective views of an imaging unit according to a second embodiment of the disclosure.
Figure 7B:
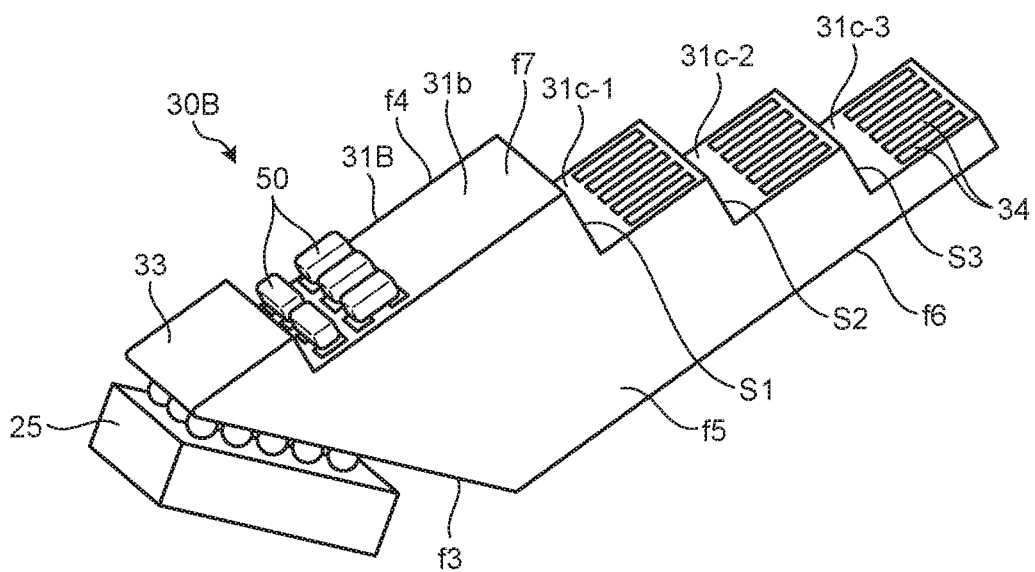

FIGS. 7A and 7B are perspective views of an imaging unit 30B according to the second embodiment of the disclosure. In the imaging unit 30B, at least a part of an electronic component mounting area 31b is a projection plane of an inclined face f3 in a vertical direction and disposed on a bottom face f7 of a rigid substrate 31B.

The rigid substrate 31B is a multi-layer substrate formed by layering a plurality of substrates, on which traces are formed, in a direction indicated by an arrow in FIG. 7A (the direction orthogonal to a plane including an endoscope axis $O_2$ and an optical axis $O_1$) (by layering the plurality of substrates parallel to an upper face f6 and the bottom face f7).

The electronic component mounting area 31b, cable mounting areas 31c-1, 31c-2, 31c-3 are formed on the bottom face f7 of the rigid substrate 31B.

A wall portion 33 is disposed on a side of the electronic component, mounting area 31b close to the inclined face f3 and steps S1, S2, S3 are provided between the electronic component mounting area 31b and the cable mounting area 31c-1, between the cable mounting area 31c-1 and the cable mounting area 31c-2, and between the cable mounting area 31c-2 and the cable mounting area 31c-3. The step S1 provided between the electronic component mounting area 31b and the cable mounting area 31c-1 does not necessarily have to be provided.

By disposing the electronic component mounting area 31b and the cable mounting areas 31c-1, 31c-2, 31c-3 on the bottom face f7, electronic components 50 and signal cables 48 can be respectively mounted at one time. By dividing the cable mounting area into the areas 31c-1, 31c-2, 31c-3 by use of the steps S2, S3, it is possible to easily connect the larger number of signal cables 48. Although the cable mounting area is divided into the three areas in the second embodiment, the cable mounting area is not necessarily divided into the three areas and may be divided into two areas.

In the second embodiment, by disposing a part of the electronic component mounting area 31b on the bottom face f7 of the rigid substrate 31B that is the projection plane of the inclined face f3 in the vertical direction, it is possible to make a length of the rigid substrate 31B in a direction of an endoscope axis $O_2$ short to thereby shorten a rigid portion of the endoscope.

According to the disclosure, by providing the area of the rigid substrate, in which the semiconductor package is mounted, on the inclined face orthogonal to the optical axis of the lens unit, it is possible to obtain the oblique-viewing endoscope in which use of a prism and the like in a special shape is unnecessary and distortion correction is unnecessary and which can be miniaturized.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An oblique-viewing endoscope comprising:
   a distal end portion having an endoscope axis extending in a longitudinal direction of the endoscope distal end portion;
   a lens having an optical axis extending in an observing direction, the endoscope axis and the optical axis forming a predetermined inclination angle with respect to each other;
   a rectangular semiconductor package comprising:
      an imaging sensor having a distal light receiving face, the imaging sensor being configured to convert an optical image projected by the lens onto the distal light receiving face into an image signal, and
      a terminal formed on a proximal face of the semiconductor package; and
   a rigid substrate comprising:
      a semiconductor package mounting area having an inclined face on which the semiconductor package is mounted, the inclined face being inclined with respect to the endoscope axis and orthogonal to the optical axis,
      an electronic component mounting area in which an electronic component is mounted, and
      a cable mounting area in which a cable is mounted,
   wherein the rigid substrate having a plurality of substrate layers forming a multi-layer substrate, the plurality of substrate layers being arranged in a layered direction parallel to a plane including the endoscope axis and the optical axis,
   at least a part of the electronic component mounting area being disposed on a triangular side surface of the rigid substrate, the triangular side surface being surrounded on a first side by the inclined face, surrounded on a second side by a projection plane of the inclined face in a horizontal direction, and surrounded on a third side by a projection plane of the inclined face in a vertical direction; and
   the electronic component being mounted on the triangular side surface.

2. The oblique-viewing endoscope according to claim 1, wherein a wall portion is disposed at one or more of the first side, second side and third side of the electronic component mounting area.

3. The oblique-viewing endoscope according to claim 1, wherein an electronic component connection land to which the electronic component is connected is disposed near a sensor electrode of the semiconductor package to which the electronic component is connected.

4. The oblique-viewing endoscope according to claim 1, wherein a cable connection land to which the cable is connected is disposed in the cable mounting area so as to shorten a trace that connects the cable connection land to a sensor electrode of the semiconductor package.

5. The oblique-viewing endoscope according to claim 1, wherein the inclined face is inclined at an angle equal to an inclination angle of a distal end surface of a distal end portion main body in which the lens is disposed.

6. The oblique-viewing endoscope according to claim 1, wherein the cable mounting area includes a first cable mounting area and a second cable mounting area and a step is provided between the first mounting area and the second mounting area.

7. The oblique-viewing endoscope according to claim 1, wherein conductive traces are arranged inside the rigid substrate, the traces electrically connecting the semiconductor package to the cable.

\* \* \* \* \*